(«2») United States Patent  (10) Patent No.: US 8,703,635 B2
Elia et al. (45) Date of Patent: Apr. 22, 2014

US008703635B2

(54) CATALYST COMPOSITION AND ITS USE THEREOF IN AROMATICS ALKYLATION

(71) Applicant: ExxonMobil Chemical Patents Inc., Baytown, TX (US)

(72) Inventors: Christine N. Elia, Bridgewater, NJ (US); Frederick Y. Lo, Middlesex, NJ (US); Jeffrey T. Elks, Geneva, IL (US); Darryl D. Lacy, Easton, PA (US); Mohan Kalyanaraman, Media, PA (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 13/909,326

(22) Filed: Jun. 4, 2013

(65) Prior Publication Data

US 2013/0267406 A1 Oct. 10, 2013

Related U.S. Application Data

(60) Division of application No. 12/520,608, filed as application No. PCT/US2007/088395 on Dec. 20, 2007, now Pat. No. 8,492,602, which is a continuation-in-part of application No. 11/654,061, filed on Jan. 16, 2007, now Pat. No. 7,381,676.

(51) Int. Cl.
*B01J 29/06* (2006.01)

(52) U.S. Cl.
USPC .............. 502/64; 502/60; 502/63; 502/67; 502/77; 502/78; 502/79

(58) Field of Classification Search
USPC ................ 502/60, 63, 64, 67, 77, 78, 79
See application file for complete search history.

(56) References Cited

U.S. PATENT DOCUMENTS

| | | | |
|---|---|---|---|
| 4,094,922 A | 6/1978 | Bartek et al. | |
| 4,302,620 A | 11/1981 | Chu | |
| 4,459,426 A | 7/1984 | Inwood et al. | |
| 4,891,458 A | 1/1990 | Innes et al. | |
| 4,954,325 A | 9/1990 | Rubin et al. | |
| 4,992,606 A | 2/1991 | Kushnerick et al. | |
| 5,144,084 A | 9/1992 | Sorensen et al. | |
| 5,236,575 A | 8/1993 | Bennett et al. | |
| 5,334,795 A | 8/1994 | Chu et al. | |
| 5,371,310 A | 12/1994 | Bennett et al. | |
| 5,430,000 A | 7/1995 | Timken | |
| 5,453,554 A | 9/1995 | Cheng et al. | |
| 5,900,508 A | 5/1999 | Eller et al. | |
| 6,337,353 B1 | 1/2002 | Lapidus et al. | |
| 6,376,730 B1 | 4/2002 | Jan et al. | |
| 2004/0111001 A1 | 6/2004 | Dandekar et al. | |
| 2004/0162454 A1 | 8/2004 | Gao et al. | |
| 2004/0266608 A1 | 12/2004 | Long et al. | |
| 2008/0027256 A1 | 1/2008 | Roth et al. | |
| 2008/0027259 A1 | 1/2008 | Roth et al. | |
| 2008/0027260 A1 | 1/2008 | Lai et al. | |

FOREIGN PATENT DOCUMENTS

| | | |
|---|---|---|
| JP | 4-227056 | 8/1992 |
| JP | 9-048746 | 2/1997 |
| WO | WO 94/29245 | 12/1994 |
| WO | WO 96/17810 | 6/1996 |
| WO | WO 99/30816 | 6/1999 |
| WO | WO 2005/070854 | 8/2005 |
| WO | WO 2006/094009 | 9/2006 |
| WO | WO 2007/143239 | 12/2007 |

OTHER PUBLICATIONS

AEROXIDE® pamphlet, http://www.aerosil.com/product/aerosol/en/products/hydrophilic-fumed-metal-oxides/Pages/default.aspx. Printed on Jun. 2, 2011.
Kim, Se-Young, "Structural Evolution of B-MCM 36 and B-ITQ-2 from B-MCM-22", Bull. Korean Chem. Soc. 2006, vol. 27, No. 10, pp. 1693-1696.
Murata et al., "*Epoxidation of propylene with molecular oxygen/methanol over a catalyst system containing palladium and Ti-modified MCM-22 without hydrogen*", Journal of Catalysis 2003, vol. 220, No. 2, pp. 513-518.
Ohtani et al., "*What is Degussa (Evonik) P25? Crystalline Composition Analysis, Reconstruction from Isolated Pure Particles and Photocatalytic Activity Test*", Journal of Photochemistry and Photobiology A: Chemistry, 2010, vol. 216, pp. 179-182.

*Primary Examiner* — Elizabeth Wood
(74) *Attorney, Agent, or Firm* — Darryl M. Tyus

(57) ABSTRACT

This disclosure relates to a catalyst composition comprising (a) MCM-22 family material; and (b) a binder comprising at least 1 wt. % of a titanium compound based on the weight of said catalyst composition, wherein said titanium compound was anatase and rutile phases.

12 Claims, No Drawings

CATALYST COMPOSITION AND ITS USE THEREOF IN AROMATICS ALKYLATION

CROSS REFERENCE TO RELATED APPLICATIONS

This application is a divisional of U.S. application Ser. No. 12/520,608, filed Jun. 22, 2009, now U.S. Pat. No. 8,492,602, which is a U.S. national stage application under 35 U.S.C. 371 of International Application PCT/US2007/088395, filed Dec. 20, 2007, which is a continuation-in-part of U.S. application Ser. No. 11/654,061, filed Jan. 16, 2007, now U.S. Pat. No. 7,381,676, the entireties of which are incorporated by reference.

FIELD

This invention relates to a novel catalyst composition, the method of manufacturing, and the process of using thereof for hydrocarbon conversions. In particular, the novel catalyst composition of this disclosure comprises a MCM-22 family material, such as MCM-49 molecular sieve and/or MCM-22 molecular sieve, and titanium compound. The hydrocarbon conversions comprise alkylation of alkylatable aromatics.

BACKGROUND OF THIS DISCLOSURE

The alkylation of aromatic hydrocarbon compounds employing zeolite catalysts is known and understood in the art. U.S. Pat. No. 5,334,795 describes the liquid phase alkylation of benzene with ethylene in the presence of MCM-22 to produce ethylbenzene; and U.S. Pat. No. 4,891,458 discloses liquid phase alkylation and transalkylation processes using zeolite beta.

Zeolite-based catalysts are used in the alkylation of benzene with propylene to produce cumene. U.S. Pat. No. 4,992,606 discloses a process for preparing cumene using MCM-22 in liquid phase.

U.S. patent application Ser. No. 11/823,129 (U.S. Publication No. 2008-0027259 A1), the entire content of which is fully incorporated by reference, discloses a crystalline molecular sieve, in its as-synthesized form, identified as EMM-10-P, a method of making EMM-10-P. In some embodiments of the U.S. patent application Ser. No. 11/823,129, the EMM-10-P has, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms. In addition, the X-ray diffraction pattern of the EMM-10-P may further include two XRD distinguishable peaks with d-spacing maxima at 11.06±0.18 and 9.25±0.13 Angstroms, wherein the peak intensity of the d-spacing maximum at 11.06±0.18 Angstroms is at least as great as the peak intensity of the d-spacing maximum at 9.25±0.13 Angstroms. Additionally, the peaks with d-spacing maxima at 11.06±0.18 and 9.25±0.13 Angstroms may be non-discrete peaks.

U.S. patent application Ser. No. 11/824,742 (U.S. Publication No. 2008-0027256 A1), the entire content of which is fully incorporated by reference, disclose novel molecular sieves designated as EMM-10, and the method making the same. In some embodiments of U.S. patent application Ser. No. 11/824,742, the EMM-10, in its ammonium exchanged form or in its calcined form, comprises unit cells with MWW topology, the crystalline molecular sieve is characterized by diffraction streaking from the unit cell arrangement in the c direction. In addition, the EMM-10 may further be characterized by the arced hk0 patterns of electron diffraction pattern. In further additional embodiments of the U.S. patent application Ser. No. 11/824,742, the EMM-10 may further be characterized by the unit cells streaking along c direction.

U.S. patent application Ser. No. 11/827,953 (U.S. Publication No. 2008-0045768 A1), the entire content of which is fully incorporated by reference, discloses a crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11. Angstroms, wherein the peak intensity of the d-spacing maximum between 12.57 to about 14.17 Angstroms is less than 90% of the peak intensity of the d-spacing maximum at 12.33±0.23 Angstroms.

A molecular sieve composition as described or characterized in U.S. patent application Ser. Nos. 11/823,129, 11/824,742, and/or 11/827,953 is designated as an EMM-10 family molecular sieve as used herein this disclosure.

The alkylation of benzene with ethylene and propylene to form ethylbenzene (EB) and cumene respectively is diffusionally limited. There is, therefore, a need to develop high activity catalyst for the alkylation of benzene with ethylene and propylene. We discovered that a composition comprising a MCM-22 family material, such as a crystalline MCM-49 molecular sieve and/or a crystalline MCM-22 molecular sieve, and titanium compound exhibits high alkylation activity.

SUMMARY OF THIS DISCLOSURE

This disclosure relates to a catalyst composition comprising (a) a MCM-22 family material, such as a crystalline MCM-49 molecular sieve and/or a crystalline MCM-22 molecular sieve; and (b) a binder comprising a titanium compound in the range from about 1 wt. % to about 35 wt. % based on the weight of the catalyst composition.

In some preferred embodiments, the MCM-22 family material of this disclosure comprises at least one of MCM-22, MCM-49, MCM-56, and EMM-10 family molecular sieve.

In one aspect of this disclosure, the titanium compound comprises at least one of titanium oxide, titanium hydroxide, titanium sulfate, titanium phosphate, or any combination thereof In another aspect of this disclosure, the catalyst composition further comprise a crystalline MCM-22 family molecular sieve having at least one of MCM-22, MCM-36, MCM-56, ITQ-1, ITQ-2, ITQ-30, PSH-3, ERB-1, SSZ-25, or any combination thereof In some embodiments of this disclosure, the catalyst composition may further comprise a non-MCM-22 family molecular sieve selected from a group consisting of a medium pore molecular sieve having a Constraint Index of 2-12 and a large pore molecular sieve having a Constraint Index of less than 2. In one embodiment, the non-MCM-22 family molecular sieve has a framework type of at least one of FAU, *BEA, MFI, MTW, or any combination thereof.

In a preferred embodiment of this disclosure, the catalyst composition of this disclosure has at least 1 wt. %, preferably at least 10 wt. %, more preferably at least 50 wt. %, even more preferably at least 65 wt. %, yet even more preferably at least 80 wt. %, of the crystalline MCM-49 molecular sieve based on the weight of the catalyst composition.

In another preferred embodiment of this disclosure, the catalyst composition of this disclosure has at least 1 wt. %, preferably at least 10 wt. %, more preferably at least 50 wt. %, even more preferably at least 65 wt. %, yet even more preferably at least 80 wt. %, of the crystalline MCM-22 molecular sieve based on the weight of the catalyst composition.

In yet another preferred embodiment of this disclosure, the catalyst composition of this disclosure has at least 1 wt. %, preferably at least 10 wt. %, more preferably at least 50 wt. %, even more preferably at least 65 wt. %, yet even more preferably at least 80 wt. %, of the MCM-22 family material based on the weight of the catalyst composition.

In yet another preferred embodiment, the catalyst composition of this disclosure has at least 5 wt. %, preferably at least 5 wt. %, most preferably at least 10 wt. %, of the titanium compound based on the weight of the catalyst composition.

In yet another preferred embodiment, the catalyst composition of this disclosure comprises a titanium compound in the range from about 1 wt. % to about 35 wt. %, preferably from about 1 wt. % to about 30 wt. %, more preferably in the range from about 5 wt. % to about 25 wt. %, based on the weight of the catalyst composition.

In some embodiments, the catalyst composition further comprises at least 5 wt. % of a molecular sieve having a *BEA framework type based on the weight of the catalyst composition.

In some aspects of this disclosure, the catalyst composition of this disclosure may further comprise an aluminum compound. In some embodiments, the aluminum compound comprises at least one of aluminum oxide, aluminum hydroxide, aluminum sulfate, aluminum phosphate, or any combination thereof. Preferably, the catalyst composition has at least 1 wt. % of the aluminum compound based on the weight of the catalyst composition. More preferably, the catalyst composition has less than 34 wt. %, preferably less than 30 wt. %, more preferably less than 20, even more preferably less than 10 wt. %, of the aluminum compound based on the weight of the catalyst composition.

In other embodiments, this disclosure relates to a process for preparing the catalyst composition of this disclosure, the process comprises (a) providing the MCM-22 family material and the binder comprising a titanium compound to form a mixture; and (b) forming the mixture into the catalyst composition, wherein the catalyst composition comprises the titanium compound in the range from about 1 wt. % to about 35 wt. % based on the total weight of the catalyst composition. In a preferred embodiment, the forming step comprises extruding. In another preferred embodiment, the catalyst composition has a shape of quadrulobe. In one embodiment, the catalyst composition used has at least 60 wt. % of the MCM-22 family material based on the weight of the catalyst composition.

In yet other embodiments, this disclosure relates to a process for preparing the catalyst composition of this disclosure, the process comprises (a) providing the crystalline MCM-49 molecular sieve and the binder comprising at least 1 wt. % of a titanium compound to form a mixture; and (b) forming the mixture into the catalyst composition. In a preferred embodiment, the forming step comprises extruding. In another preferred embodiment, the catalyst composition has a shape of quadrulobe. In one embodiment, the catalyst composition used has at least 60 wt. % of the crystalline MCM-49 molecular sieve based on the weight of the catalyst composition.

In another embodiment, this disclosure discloses a process for alkylating an aromatic hydrocarbon with an alkylating agent to produce an alkylated aromatic product, the process comprises contacting the aromatic hydrocarbon and the alkylating agent with the catalyst composition under alkylation conditions effective to alkylate the aromatic hydrocarbon with the alkylating agent to form an effluent comprising the alkylated aromatic product. In a preferred embodiment, the alkylation conditions are maintained to ensure the alkylation process operated in at least partial liquid phase. The term "at least partial liquid phase" as used herein, means that at least 1 wt. %, preferably at least 5%, more preferably at least 10%, even more preferably at least 50%, and most preferably at least 90%, of the combined aromatic hydrocarbon and alkylating agent (at the feed point of the alkylation zone), or the combined aromatic hydrocarbon, alkylating agent, and the alkylated aromatic product (at any point after the feed point of the alkylation zone) is in liquid phase based on the total weight of the combined aromatic hydrocarbon, alkylating agent, and the alkylated aromatic product. In some preferred embodiments, the aromatic hydrocarbon comprises benzene, the alkylating agent comprises ethylene, and the alkylated aromatic product comprises ethylbenzene. In other preferred embodiments, the aromatic hydrocarbon comprises benzene, the alkylating agent comprises propylene, and the alkylated aromatic product comprises cumene. In some embodiments, the effluent produced by the process of this disclosure comprises the alkylated aromatic product which is at least 1 wt. %, preferably at least 5 wt. %, even more preferably at least 10 wt. %, and most preferably at least 20 wt. %, greater than the amount of alkylated aromatic product in a effluent produced by contacting an alumina-bound-catalyst composition having a binder consisting of alumina and same weight ratio of the molecular sieve over the alumina-bound-catalyst composition under same alkylation conditions. In some embodiments, the catalytic activity (measured by benzene alkylation with propylene under the reaction conditions of temperature 130° C. and pressure 2170 kPa-a as demonstrated in the examples) of the catalyst composition of this disclosure is at least 5%, preferable at least 10%, even more preferable at least 20%, yet even more preferable at least 40%, and most preferable at least 60%, greater than the catalytic activity (measured by benzene alkylation with propylene under the reaction conditions of temperature 130° C. and pressure 2170 kPa-a as demonstrated in the examples) of an alumina-bound-catalyst composition having a binder consisting of alumina under equivalent alkylation conditions and same weight ratio of the molecular sieve to the alumina-bound-catalyst composition.

DETAILED DESCRIPTION OF THIS DISCLOSURE

Introduction

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;
(ii) molecular sieves made from a common second degree building block, a 2-dimensional tiling of such MWW framework type unit cells, forming a "monolayer of one unit cell thickness", preferably one c-unit cell thickness;
(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or
(iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), UZM-8 (described in U.S. Pat. No. 6,756,030), EMM-10 family molecular sieve comprised of at least one of the materials as disclosed in U.S. patent application Ser. Nos. 11/823,129, 11/824,742, and 11/827,953, and MCM-56 (described in U.S. Pat. No. 5,362,697). The entire contents of the patents are incorporated herein by reference.

It is to be appreciated that the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, ITQ-2, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, ITQ-2, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase transalkylation conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite, zeolite Omega, and a material having an X-ray diffraction pattern including d-spacing maxima at 12.4±0.25, 6.9±0.15, 3.57±0.07 and 3.42±0.07 Angstroms.

The EMM-10 family molecular sieve comprises at least one of the materials as disclosed in U.S. patent application Ser. Nos. 11/823,129, 11/824,742, and 11/827,953.

The EMM-10 family molecular sieve as disclosed in U.S. patent application Ser. No. 11/823,129 is EMM-10-P. An EMM-10-P molecular sieve is a crystalline molecular sieve having, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms.

In addition, the X-ray diffraction pattern of the EMM-10-P molecular sieve may further include two XRD distinguishable peaks with d-spacing maxima at 11.06±0.18 and 9.25±0.13 Angstroms, wherein the peak intensity of the d-spacing maximum at 11.06±0.18 Angstroms is at least as great as the peak intensity of the d-spacing maximum at 9.25±0.13 Angstroms. Additionally, the peaks with d-spacing maxima at 11.06±0.18 and 9.25±0.13 Angstroms may be non-discrete peaks.

In a preferred embodiment, the EMM-10-P molecular sieve is a crystalline MCM-22 family molecular sieve that has a total surface area of greater than 450 m$^2$/g as measured by the N$_2$ BET method. The crystalline MCM-22 family molecular sieve of EMM-10-P preferably has a ratio of the external surface area over the total surface area of less than 0.15 after conversion into H-form by exchange with ammonium nitrate and calcination, wherein the external surface area is determined from a t-plot of the N$_2$ BET.

In yet further additional embodiments, the EMM-10-P molecular sieve has a morphology of tabular habit, wherein at least 50 wt. % of the EMM-10-P molecular sieve have a crystal diameter greater than 1 μm as measured by the SEM, preferably greater than 2 pm as measured by the SEM.

In some aspects, the EMM-10-P molecular sieve has a morphology of tabular habit, wherein at least 50 wt. % of the EMM-10-P molecular sieve have a crystal thickness of about 0.025 μm as measured by the SEM.

A method of making an EMM-10-P molecular sieve comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity, preferably 10 to 10000, more preferably from 10 to 55;
H$_2$O:Y=1 to 10000, preferably 1 to 5000, more preferably from 5 to 35;
OH$^-$:Y without trivalent element source correction=0.001 to 0.59, and/or
OH$^-$:Y (with trivalent element source correction)=0.001 to 0.39

M$^+$:Y=0.001 to 2, preferably from 0.1 to 1;
R:Y=0.001 to 2, preferably from 0.1 to 1;
wherein M is an alkali metal and R is at least one N,N,N,N'N'N'-hexamethyl-1,5-pentanediaminium salt (Me$_6$-diquat-5 salt(s)), preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, Me$_6$-diquat-5 hydroxide bromide, Me$_6$-diquat-5 hydroxide chloride, Me$_6$-diquat-5 hydroxide fluoride, Me$_6$-diquat-5 hydroxide iodide, Me$_6$-diquat-5 hydroxide nitrate, Me$_6$-diquat-5 fluoride bromide, Me$_6$-diquat-5 fluoride chloride, Me$_6$-diquat-5 fluoride iodide, Me$_6$-diquat-5 fluoride nitrate, Me$_6$-diquat-5 chloride bromide, Me$_6$-diquat-5 chloride iodide, Me$_6$-diquat-5 chloride nitrate, Me$_6$-diquat-5 iodide bromide, Me$_6$-diquat-5 bromide nitrate, and any mixtures thereof, more preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, and any mixtures thereof, most preferably R is Me$_6$-diquat-5 dibromide; and (b) submitting the mixture at crystallization conditions to form a product comprising the desired EMM-10-P molecular sieve, wherein the crystallization conditions comprise a temperature in the range of from 100° C. to 200° C., preferably from about 140 to about 180 C; and a crystallization time from about 1 hour to 400 hours, preferably from about 1 to 200 hours, optionally a stirring speed in the range of from 0 to 1000 RPM, preferably from 0 to 400 RPM.

Another method of making an EMM-10-P molecular sieve comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity, preferably 10 to 10000, more preferably from about 10 to 55;
H$_2$O:Y=1 to 10000, preferably 1 to 5000, more preferably from 5 to 35;
OH$^-$:Y without trivalent element source correction=0.61 to 0.72 and/or
OH$^-$:Y with trivalent element source correction=0.41 to 0.49 or 0.51 to 0.62
M$^+$:Y=0.001 to 2, preferably from 0.1 to 1;
R:Y=0.001 to 2, preferably from 0.1 to 1;
wherein M is an alkali metal and R is at least one N,N,N,N'N'N'-hexamethyl-1,5-pentanediaminium salt (Me$_6$-diquat-5 salt(s)), preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, Me$_6$-diquat-5 hydroxide bromide, Me$_6$-diquat-5 hydroxide chloride, Me$_6$-diquat-5 hydroxide fluoride, Me$_6$-diquat-5 hydroxide iodide, Me$_6$-diquat-5 hydroxide nitrate, Me$_6$-diquat-5 fluoride bromide, Me$_6$-diquat-5 fluoride chloride, Me$_6$-diquat-5 fluoride iodide, Me$_6$-diquat-5 fluoride nitrate, Me$_6$-diquat-5 chloride bromide, Me$_6$-diquat-5 chloride iodide, Me$_6$-diquat-5 chloride nitrate, Me$_6$-diquat-5 iodide bromide, Me$_6$-diquat-5 bromide nitrate, and any mixtures thereof, more preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, and any mixtures thereof, most preferably R is Me$_6$-diquat-5 dibromide; and (b) submitting the mixture at crystallization conditions to form a product comprising the desired EMM-10-P molecular sieve, wherein the crystallization conditions comprise a temperature in the range of from 100° C. to 200° C., preferably from about 140 to about 180 C; and a crystallization time from about 1 hour to 400 hours, preferably from about 1 to 200 hours, optionally a stirring speed in the range of from 0 to 1000 RPM, preferably from 0 to 400 RPM.

Yet another method of making an EMM-10-P molecular sieve comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity, preferably 10 to 10000, more preferably from 10 to 55;
H$_2$O:Y=1 to 35, preferably from 5 to 35;
OH$^-$:Y=0.001 to 2, preferably from 0.01 to 0.5;
M$^+$:Y=0.001 to 2, preferably from 0.1 to 1;
R:Y=0.001 to 2, preferably from 0.1 to 1;
wherein M is an alkali metal and R is at least one N,N,N,N'N'N'-hexamethyl-1,5-pentanediaminium salt (Me$_6$-diquat-5 salt(s)), preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, Me$_6$-diquat-5 hydroxide bromide, Me$_6$-diquat-5 hydroxide chloride, Me$_6$-diquat-5 hydroxide fluoride, Me$_6$-diquat-5 hydroxide iodide, Me$_6$-diquat-5 hydroxide nitrate, Me$_6$-diquat-5 fluoride bromide, Me$_6$-diquat-5 fluoride chloride, Me$_6$-diquat-5 fluoride iodide, Me$_6$-diquat-5 fluoride nitrate, Me$_6$-diquat-5 chloride bromide, Me$_6$-diquat-5 chloride iodide, Me$_6$-diquat-5 chloride nitrate, Me$_6$-diquat-5 iodide bromide, Me$_6$-diquat-5 bromide nitrate, and any mixtures thereof, more preferably R is selected from the group consisting of Me$_6$-diquat-5 dibromide, Me$_6$-diquat-5 dichloride, Me$_6$-diquat-5 difluoride, Me$_6$-diquat-5 diiodide, Me$_6$-diquat-5 dihydroxide, Me$_6$-diquat-5 sulfate, Me$_6$-diquat-5 dinitrate, and any mixtures thereof, most preferably R is Me$_6$-diquat-5 dibromide, wherein the OH$^-$:Y is calculated with or without trivalent element source correction; and (b) submitting the mixture at crystallization conditions to form a product comprising the desired EMM-10-P molecular sieve, wherein the crystallization conditions comprise a temperature in the range of from 100° C. to 200° C., preferably from about 140 to about 180 C; and a crystallization time from about 1 hour to 400 hours, preferably from about 1 to 200 hours, optionally a stirring speed in the range of from 0 to 1000 RPM, preferably from 0 to 400 RPM.

The EMM-10 family molecular sieve as disclosed in U.S. patent application Ser. No. 11/824,742 is EMM-10. An EMM-10 molecular sieve is a crystalline molecular sieve, in its ammonium exchanged form or in its calcined form, comprising unit cells with MWW topology, the crystalline molecular sieve is characterized by diffraction streaking from the unit cell arrangement in the c direction.

In additional embodiments, the EMM-10 molecular sieve may further be characterized by the arced hk0 patterns of electron diffraction pattern.

In further additional embodiments, the EMM-10 molecular sieve may further be characterized by the unit cells streaking along c direction.

In yet further additional embodiments, the EMM-10 molecular sieve may further be characterized by the double unit cell along c direction.

In yet more embodiments, the EMM-10 molecular sieve is a crystalline MCM-22 family molecular sieve has a total surface area of greater than 450 m$^2$/g as measured by the N$_2$ BET method. The crystalline MCM-22 family molecular sieve has a ratio of the external surface area over the total surface area of less than 0.15 after conversion into H-form by exchange with ammonium nitrate and calcination, wherein the external surface area is determined from a t-plot of the N$_2$ BET.

In yet some additional embodiments, the EMM-10 molecular sieve may have a morphology of tabular habit, wherein at least 50 wt. % of the EMM-10 molecular sieve having a crystal diameter greater than 1 μm as measured by the SEM.

In some aspect, the EMM-10 molecular sieve has a morphology of tabular habit, wherein at least 50 wt. % of the EMM-10 molecular sieve having a crystal thickness of about 0.025 μm as measured by the SEM.

An EMM-10 molecular sieve may be made by recovering an EMM-P-10 molecular sieve followed by treating the recovered EMM-10-P molecular sieve by:
(1) ion-exchanging the EMM-10-P molecular sieve with an ammonium salt(s) solution;
(2) calcining the EMM-10-P molecular sieve under calcination conditions; or
(3) ion-exchanging the EMM-10-P molecular sieve with an ammonium salt(s) solution and calcining the ion-exchanged EMM-10-P molecular sieve under calcination conditions.

The EMM-10 family molecular sieve as disclosed in U.S. patent application Ser. No. 11/827953 is a crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11. Angstroms, wherein the peak intensity of the d-spacing maximum between 12.57 to about 14.17 Angstroms is less than 90% of the peak intensity of the d-spacing maximum at 12.33±0.23 Angstroms.

In some embodiments, the EMM-10 family molecular sieve as disclosed in U.S. patent application Ser. No. 11/827,953 may be made by a method comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity
H$_2$O:Y=1 to 10000
OH$^-$:Y without trivalent element source correction=0.001 to 0.59, and/or OH$^-$:Y (with trivalent element source correction)=0.001 to 0.39
M$^+$:Y=0.001 to 2
R:Y=0.001 to 2
wherein M is an alkali metal and R is at least one N,N,N,N'N'N'-hexamethyl-1,5-pentanediaminium salt(s), N,N,N,N'N'N' -hexamethyl-1,6-hexanediaminium salt(s), or any combination thereof, wherein the OH$^-$:Y is calculated; and
(b) submitting the mixture at crystallization conditions to form a product comprising the desired crystalline molecular sieve, wherein the crystallization conditions comprise a temperature in the range of from 100° C. to 250° C., a stirring speed of ranging from at least 150 RPM to less than 5000 RPM, and a crystallization time from about 1 hour to 400 hours; and
(c) recovering the crystalline molecular sieve.

In yet other embodiments, the EMM-10 family molecular sieve as disclosed in U.S. patent application Ser. No. 11/827, 953 may be made by a method comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity
H$_2$O:Y=1 to 10000
OH$^-$:Y without trivalent element source correction=0.74 to 2 and/or OH$^-$:Y with trivalent element source correction=0.64 to 2
M$^+$:Y=0.001 to 2
R:Y=0.001 to 2
wherein M is an alkali metal and R is at least one N,N,N,N'N'N'-hexamethyl-1,5-pentanediaminium salt(s), N,N,N,N'N'N' -hexamethyl-1,6-hexanediaminium salt(s), or any combination thereof, wherein the OH$^-$:Y is calculated without trivalent element source correction; and
(b) submitting the mixture at crystallization conditions to form a product comprising the desired crystalline molecular sieve, wherein the crystallization conditions comprise a temperature in the range of from 100° C. to 200° C., a stirring speed of ranging from at least 150 RPM to less than 5000 RPM, and a crystallization time from about 1 hour to 400 hours; and
(c) recovering the crystalline molecular sieve.

In yet other embodiments, the EMM-10 family molecular sieve as disclosed in U.S. patent application Ser. No. 11/827, 953 may be made by a method comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), the mixture having the following molar ratio:
Y:X$_2$=10 to infinity
H$_2$O:Y=5 to 35
OH$^-$:Y=0.001 to 2
M$^+$:Y=0.001 to 2
R:Y=0.001 to 2
wherein M is an alkali metal and R is at least one N,N,N,N'N'N'-hexamethyl-1,5-pentanediaminium salt(s), N,N,N,N'N'N' -hexamethyl-1,6-hexanediaminium salt(s), or any combination thereof, wherein the OH$^-$:Y is calculated with or without trivalent element source correction; and
(b) submitting the mixture at crystallization conditions to form a product comprising the desired crystalline molecular sieve, wherein the crystallization conditions comprise a temperature in the range of from 100° C. to 200° C., a stirring speed of ranging from at least 150 RPM to less than 5000 RPM, and a crystallization time from about 1 hour to 400 hours; and (c) recovering the crystalline molecular sieve.

In yet other embodiments, the EMM-10 family molecular sieve as disclosed in U.S. patent application Ser. No. 11/827,953 may be made by a method comprising the steps of:

(a) providing a mixture comprising at least one source of at least one tetravalent element (Y), at least one source of at least one alkali or alkali earth metal element, at least one directing-agent (R), water, at least one seed, and optionally at least one source of at least one trivalent element (X), the mixture having the following molar ratio:

$Y:X_2$=10 to infinity
$H_2O:Y$=1 to 10000
$OH^-:Y$=0.001 to 2
$M^+:Y$=0.001 to 2
$R:Y$=0.001 to 2 wherein M is an alkali metal and R is at least one N,N,N,N'N'N'-hexamethyl-1,5-pentanediaminium salt(s), N,N,N,N'N'N' -hexamethyl-1,6-hexanediaminium salt(s), or any combination thereof, wherein the $OH^-:Y$ is calculated with or without trivalent element source correction, wherein the seed has a concentration in the mixture ranging from about 0.01 to 10 wt. % based on the weight of the tetravalent element oxide in the mixture; and (b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and (c) recovering the crystalline molecular sieve.

In yet other embodiments, the EMM-10 family molecular sieve as disclosed in U.S. patent application Ser. No. 11/827,953 may be made by a method comprising the steps of:

(a) providing a mixture comprising at least one source of at least one non-germanium tetravalent element (Y), at least one source of germanium (Ge), at least one directing-agent (R), water, and optionally at least one source of at least one trivalent element (X) and at least one source of at least one alkali or alkali earth metal element, the mixture having the following molar ratio:

$(Ge+Y):X_2$=10 to infinity
$H_2O:Y$=1 to 10000
$M^+:Y$=0 to 2
$R:Y$=0.001 to 2 wherein M is an alkali metal and R comprises at least one N,N,N,N'N'N'-hexamethyl-1,5-pentanediaminium salt(s), N,N,N,N'N'N'-hexamethyl-1,6-hexanediaminium salt(s), or any combination thereof; and (b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and (c) recovering the crystalline molecular sieve.

As used herein, an "alkylatable aromatic compound" is a compound that may receive an alkyl group and an "alkylating agent" is a compound which may donate an alkyl group.

The term "wppm" as used herein is defined as parts per million by weight.

All weights of molecular sieve, weights of binder, and weights of catalyst composition, as used in this disclosure, are calcined based weight (at 510° C. in air for at least one hour).

The term "aromatic" as used herein is to be understood in accordance with its art-recognized scope which includes alkyl-substituted and unsubstituted mono- and polynuclear compounds. Compounds of an aromatic character, which possess a heteroatom, are also useful provided sufficient activity can be achieved if they act as catalyst poisons under the reaction conditions selected. A non-exclusive list of examples of aromatic compounds includes benzene and toluene.

Catalyst

The catalyst composition of this disclosure comprises (a) a MCM-22 family material, such as a crystalline MCM-49 molecular sieve and/or a MCM-22 molecular sieve; and (b) a binder comprising a titanium compound in the range from about 1 wt. % to about 35 wt. % based on the weight of the catalyst composition.

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). The MCM-22 family materials of this disclosure are preferably substantially free of non-MCM-22 family material(s). The term "substantially free of non-MCM-22 family material(s)" used herein means the MCM-22 family material of this disclosure preferably contains a minor proportion (less than 50 wt. %), preferably less than 20 wt. %, more preferably less than 10 wt. %, even more preferably less than 5 wt. %, and most preferably less than 1 wt. %, of non-MCM-22 family materials ("impurities") in the MCM-22 family materials, which weight percent (wt. %) values are based on the combined weight of impurities and pure phase MCM-22 family materials.

The MCM-22 family material comprises crystalline MCM-22 family molecular sieve, such as, MCM-22, MCM-49, MCM-56, EMM-10 family molecular sieve. Preferably, the MCM-22 family material of this disclosure comprises at least one of MCM-22, MCM-49, MCM-56, and EMM-10 family molecular sieve.

The crystalline MCM-22 family molecular sieve has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, the material has a formula, on an anhydrous basis and in terms of moles of oxides per n moles of $YO_2$, as follows:

$$(0.005-1)M_2O:(1-4)R:X_2O_3:nYO_2$$

wherein M is an alkali or alkaline earth metal, and R is an organic moiety. The M and R components are associated with the material as a result of their presence during synthesis, and are typically removed by post-synthesis methods well known to those skilled in the art and/or hereinafter more particularly described.

In some embodiments, the crystalline MCM-22 family molecular sieve of this disclosure comprises at least one of MCM-22, MCM-36, MCM-49, EMM-10 family molecular sieve, MCM-56, ITQ-1, ITQ-2, ITQ-30, an intergrowth-phase thereof, or a mix phase thereof In a preferred embodiment of this disclosure, the catalyst composition of this disclosure has at least 1 wt. %, preferably at least 10 wt. %, more preferably at least 50 wt. %, even more preferably at least 65 wt. %, of the crystalline MCM-22 family molecular sieve based on the weight of the catalyst composition.

The crystalline MCM-22 family molecular sieve of this disclosure may contain less than 10 wt. %, preferably less than 5 wt. %, even more preferably less than 1 wt. %, based on the weight of the crystalline molecular sieve composition, of non-MCM-22 family molecular sieve(s). Typical examples of the non-MCM-22 family molecular sieve(s) co-existing with the MCM-22 family molecular sieve(s) of this disclosure are Kenyaite, EU-1, ZSM-50, ZSM-12, ZSM-48, ZSM-5, Ferrierite, Mordenite, Solalite, and/or Analcine. Other examples of the non-MCM-22 family molecular sieve(s) co-existing with the MCM-22 family molecular sieve(s) of this disclosure are molecular sieves having framework type of EUO, MTW, FER, MOR, SOD, ANA, and/or MFI. The product of the synthesis may comprises less than 10 wt. %, preferably less than 5 wt. %, even more preferably less than 1 wt. %, based on the weight of the product, of non-crystalline materials, e.g., quartz.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof Particularly preferred cations are those which tailor the catalytic activity for certain hydrocarbon conversion reactions. These include hydrogen, rare earth metals and metals of Groups 1-17, preferably Groups 2-12 of the Periodic Table of the Elements.

The titanium compound includes, but not limited to, at least one of titanium oxide, titanium hydroxide, titanium sulfate, titanium phosphate, titanium alkoxides or any combination thereof In some embodiments, the catalyst composition of this disclosure comprises at least 1 wt. %, preferably at least 5 wt. %, more preferably at least 10 wt. %, sometimes at least 15 wt. % or at least 20 wt. %, of the titanium compound based on the weight of the catalyst composition.

In other embodiments, the catalyst composition of this disclosure comprises a titanium compound in the range from about 1 wt. % to about 35 wt. % based on the weight of the catalyst composition. The following weight percentages are useful lower limits for the weight percentage of the titanium compound in the catalyst composition based on the weight of the catalyst composition: 1, 2, 3, 4, 5, 10, 15, 20, 25, and 30. The following weight percentages are useful upper limits for the weight percentage of the titanium compound in the catalyst composition based on the weight of the catalyst composition: 2, 3, 4, 5, 6, 10, 11, 15, 16, 20, 21, 25, 26, 30, 31 and 35. The weight percentage of the titanium compound in the catalyst composition based on the weight of the catalyst composition ideally falls in a range between any one of the above-mentioned lower limits and any one of the above-mentioned upper limits, so long as the lower limit is less than or equal to the upper limit.

In some embodiments, the catalyst composition may further comprise a non-MCM-22 family molecular sieve selected from a group consisting of a medium pore molecular sieve having a Constraint Index of 2-12 and a large pore molecular sieve having a Constraint Index of less than 2. In one embodiment, the non-MCM-22 family molecular sieve has a framework type of at least one of FAU, *BEA, MFI, MTW, or any combination thereof. In some embodiments, the catalyst composition further comprises at least 5 wt. % of a molecular sieve having a *BEA framework type based on the weight of the catalyst composition.

Suitable medium pore molecular sieves having a Constraint Index of 2-12 (as defined in U.S. Pat. No. 4,016,218), include ZSM-5, ZSM-11, ZSM-12, ZSM-22, ZSM-23, ZSM-35, and ZSM-48. ZSM-5 is described in detail in U.S. Pat. No. 3,702,886 and Reissue Pat. No. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite beta is described in U.S. Pat. No. 3,308,069, and Reissue Pat. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the constraint index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which Constraint Index may be determined is described fully in U.S. Pat. No. 4,016,218, which is incorporated herein by reference.

The stability of the catalyst(s) used in the present process may be increased by steaming U.S. Pat. Nos. 4,663,492; 4,594,146; 4,522,929; and 4,429,176, describe conditions for the steam stabilization of zeolite catalysts which may be utilized to steam-stabilize the catalyst. Reference is made to these patents for a detailed description of the steam stabilization technique for use with the present catalysts. The steam stabilization conditions typically include contacting the catalyst with, e.g., 5%-100% steam at a temperature of at least about 300° C. (e.g., 300° -650° C.) for at least one hour (e.g., 1-200 hours) at a pressure of 101-2,500 kPa-a (kilopascal-absolute). In a more particular embodiment, the catalyst may be made to undergo steaming with 75%-100% steam at 315° C.-500° C. and atmospheric pressure for 2-25 hours. The steaming of the catalyst may take place under conditions sufficient to initially increase the Alpha Value of the catalyst, the significance of which is discussed below, and produce a steamed catalyst having an enhanced Alpha Value. If desired, steaming may be continued to subsequently reduce the Alpha Value from the higher Alpha Value to an Alpha Value which is substantially the same as the Alpha Value of the unsteamed catalyst.

The alpha value test is a measure of the cracking activity of a catalyst and is described in U.S. Pat. No. 3,354,078 and in the *Journal of Catalysis*, Vol. 4, p. 527 (1965); Vol. 6, p. 278

(1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

In some aspects of this disclosure, the catalyst composition of this disclosure may further comprise an aluminum compound. In some embodiments, the aluminum compound comprises at least one of aluminum oxide, aluminum hydroxide, aluminum sulfate, aluminum phosphate, or any combination thereof. Preferably, the catalyst composition has at least 1 wt. % of the aluminum compound based on the weight of the catalyst composition.

In yet other embodiments, this disclosure relates to a process for preparing the catalyst composition of this disclosure, the process comprises (a) providing the crystalline MCM-22 family molecular sieve and the binder comprising at least 1 wt. % of a titanium compound to form a mixture; and (b) forming the mixture into the catalyst composition. In a preferred embodiment, the crystalline MCM-22 family molecular sieve comprises at least one of MCM-22, MCM-49, and MCM-56. The catalyst prepared by the instant invention can be shaped into a wide variety of particle sizes. Generally speaking, the particles can be in the form of a powder, a granule, or a molded product, such as an extrudate. In cases where the catalyst is molded, such as by extrusion, the catalyst can be extruded before drying or partially dried and then extruded. In a preferred embodiment, the forming step comprises extruding. In another preferred embodiment, the catalyst composition has a shape of quadrulobe. In one embodiment, the catalyst composition used in the has at least 60 wt. %, preferably at least 65 wt. %, more preferably at least 80 wt. %, of the crystalline MCM-22 family molecular sieve based on the weight of the catalyst composition.

In other embodiments, this disclosure relates to a process for preparing the catalyst composition of this disclosure, the process comprises (a) providing the MCM-22 family material and the binder comprising a titanium compound to form a mixture; and (b) forming the mixture into the catalyst composition, wherein the catalyst composition comprises the titanium compound in the range from about 1 wt. % to about 35 wt. % based on the total weight of the catalyst composition. In a preferred embodiment, the crystalline MCM-22 family molecular sieve comprises at least one of MCM-22, MCM-49, and MCM-56.

In a preferred embodiment, the forming step comprises extruding. In another preferred embodiment, the catalyst composition has a shape of quadrulobe. In one embodiment, the catalyst composition used has at least 60 wt. % of the MCM-22 family material based on the weight of the catalyst composition.

Conventional methods can be used to form the catalyst particles. Such methods generally include the steps of mixing batch materials, which have as their main constituents molecular sieve and binder, blending the mixture, forming or shaping the batch into a green body, drying, and subsequently calcining the green body to form the support. Usually the forming is undertaken via extrusion or via other methods that require the application of pressure and/or heat. It is conventional to add such additives as extrusion aids, plasticizers, and burnout agents (e.g. graphite) to the batch during the mixing step. Polymers, such as polyvinylalcohol (PVA), can be utilized as extrusion aids. In an embodiment, PVA is used as an extrusion aid in levels from 0.01 to 5 wt. % where the PVA is added during the mixing step.

The addition of titania as a binder or co-binder results in catalyst that is smooth, has little surface texture and shows higher activity. Degussa's P25 Titania, a mixture of rutile and anatase phases, is applicable for this process.

The advantage of the catalyst composition disclosed in this disclosure is the high activity for alkylation reaction. The manufacturing process of the catalyst composition is simple. Use of the smaller particle, spherical-shaped titania solids also aids in the forming process used to produce extrudates. In some embodiments, the catalyst composition may further comprise a material resistant to the temperatures and other conditions employed in organic conversion processes. Such materials include clays, silica and/or metal oxides such as alumina The latter may be either naturally occurring or in the form of gelatinous precipitates or gels including mixtures of silica and metal oxides. These materials may be incorporated into naturally occurring clays, e.g., bentonite and kaolin, to improve the crush strength of the catalyst under commercial operating conditions. The materials, i.e. clays, oxides, etc., function as binders for the catalyst. It is desirable to provide a catalyst having good crush strength because in commercial use it is desirable to prevent the catalyst from breaking down into powder-like materials.

Naturally occurring clays which can be composited with the crystalline molecular sieve include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the crystalline molecular sieve can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline molecular sieve and inorganic oxide matrix vary widely, with the crystal content ranging from about 1 to about 99 percent by weight and more usually, particularly when the composite is prepared in the form of beads, in the range of about 20 to about 80 wt. % of the composite.

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known forming techniques, like spray drying, prilling, pelletizing and extrusion, have been and are being used to produce macrostructures in the form of, for example, spherical particles, extrudates, pellets and Tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

Alkylation Reactions

In another embodiment, this disclosure discloses a process for alkylating an aromatic hydrocarbon with an alkylating agent to produce an alkylated aromatic product, the process comprises contacting the aromatic hydrocarbon and the alkylating agent with the catalyst composition of this disclosure under alkylation conditions effective to alkylate the aromatic hydrocarbon with the alkylating agent to form an effluent comprising the alkylated aromatic product. In some preferred embodiments, the aromatic hydrocarbon comprises benzene, the alkylating agent comprises ethylene, and the alkylated aromatic product comprises ethylbenzene. In other preferred embodiments, the aromatic hydrocarbon comprises benzene, the alkylating agent comprises propylene, and the alkylated aromatic product comprises cumene.

The catalyst composition of this disclosure is also a useful catalyst for transalkylations, such as, for example, polyalkylbenzene transalkylations.

Substituted aromatic compounds which may be used for the invention should possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic compounds that may be used for this invention include benzene, naphthalene, anthracene, naphthacene, perylene, coronene, and phenanthrene, with benzene being preferred.

Suitable alkyl substituted aromatic compounds that may be used for this invention include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate streams that may contain substantial quantities of benzene, toluene and/or xylene may be particularly suitable feed for the process of this invention. Although the process is particularly directed to the production of ethylbenzene from polymer grade and dilute ethylene, it is equally applicable to the production of other $C_7$-$C_{20}$ alkylaromatic compounds, such as cumene, as well as $C_6$+ alkylaromatics, such as $C_8$-$C_{16}$ linear and near linear alkylbenzenes.

Suitable alkylating agent(s) that may be used in this invention comprise alkene compound(s) and/or alcohol compound(s), and mixtures thereof. Other suitable alkylating agents that may be useful in the process of this invention generally include any aliphatic or aromatic organic compound having one or more available alkylating aliphatic groups capable of reaction with the alkylatable aromatic compound. Examples of suitable alkylating agents are $C_2$-$C_{16}$ olefins such as $C_2$-$C_5$ olefins, viz., ethylene, propylene, the butenes, and the pentenes; $C_1$-$C_{12}$ alkanols (inclusive of monoalcohols, dialcohols, trialcohols, etc.), preferably $C_1$-$C_5$ alkanols, such as methanol, ethanol, the propanols, the butanols, and the pentanols; $C_2$-$C_{20}$ ethers, e.g., $C_2$-$C_5$ ethers including dimethylether and diethylether; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth. It is generally preferred that the alkylating agent has no greater than 5 carbon atoms, more preferably no greater than 3 carbon atoms. Thus the alkylating agent may preferably be selected from the group consisting of $C_2$-$C_5$ olefins and $C_1$-$C_5$ alkanols. The alkylating agent includes a concentrated alkene feedstock (e.g., polymer grade olefins) and a dilute alkene feedstock (e.g., catalytic cracking off-gas).

Suitable alkyl substituted aromatic compounds which may be prepared from the alkylation process of the present invention include toluene, xylene, isopropylbenzene (cumene), normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethyl,anthracene; 9-ethylanthracene; 2-methylanthracene; o-methylanthracene; 9,10-dimethylphenanthrene; and 3-methyl-phenanthrene. Preferably, the alkylated aromatic product comprises monoalkylbenzene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{16}$.

The alkylation reaction is carried out with the alkylatable aromatic compound and the alkylating agent in the reaction zone under alkylation or transalkylation conditions. The alkylation or transalkylation conditions include a temperature of 100 to 285° C. and a pressure of 689 to 4601 kPa-a, preferably, a pressure of 1500 to 3000 kPa-a, a WHSV based on alkylating agent (e.g., alkene) for overall reactor of 0.1 to 10 $hr^{-1}$, preferably, 0.2 to 2 $hr^{-1}$, more preferably, 0.5 to 1 $hr^{-1}$, or a WHSV based on both alkylating agent and alkylatable aromatics for overall reactor of 10 to 100 $hr^{-1}$, preferably, 20 to 50 $hr^{-1}$. The alkylatable aromatic compound is alkylated with the alkylating agent (e.g., alkene) in the presence of an alkylation or transalkylation catalyst in a reaction zone or a plurality of reaction zones. The reaction zone(s) are preferably located in a single reactor vessel, but may include another reaction zone having an alkylation or transalkylation catalyst bed, located in separate vessel which may be a bypassable and which may operate as a reactive guard bed. The catalyst composition used in the reactive guard bed may be different from the catalyst composition used in the reaction zone. The catalyst composition used in the reactive guard bed may have multiple catalyst compositions. At least one reaction zone, and normally each reaction zone, is maintained under conditions effective to cause alkylation of the alkylatable aromatic compound with the alkylating agent in the presence of an alkylation or transalkylation catalyst.

The effluent from the reaction zone comprises the desired alkylated aromatic product, unreacted alkylatable aromatic compound, any unreacted alkylating agent (e.g., alkene, alkene conversion is expected to be at least 90 mol.%, preferably, about 98-99.9999 mol.%) and the alkane component and the other impurities. In one embodiment, at least a portion of the effluent is fed to another reaction zone where an alkylating agent is added for reaction with the unreacted alkylatable aromatic compound with an alkylation or transalkylation catalyst. Furthermore, at least a portion the effluent from any of the reaction zone(s) may be fed directly or indirectly to a transalkylation unit. In some embodiments, the amount of the alkylated aromatic product produced by the process of this disclosure is at least 1 wt. %, preferable at least 5 wt. %, even more preferable at least 10 wt. %, and most preferable at least 20 wt. %, greater than the amount of alkylated aromatic product in a effluent produced by contacting an alumina-bound-catalyst composition having a binder consisting of alumina and same weight ratio of the molecular sieve over the alumina-bound-catalyst composition.

In addition to, and upstream of, the reaction zones, a by-passable reactive or unreactive guard bed may normally be located in a reactor separate from the alkylation reactor. Such guard bed may also be loaded with an alkylation or transalkylation catalyst, which may be the same or different from the catalyst used in the reaction zone(s). Such guard bed is maintained from under ambient conditions, or at suitable alkylation or transalkylation conditions. At least a portion of alkylatable aromatic compound, and optionally at least a portion of the alkylating agent, are passed through the unreactive or reactive guard bed prior to entry into the reaction zone. These guard beds not only serve to affect the desired alkylation reaction, but is also used to remove any reactive impurities in the feeds, such as nitrogen compounds, which could otherwise poison the remainder of the alkylation or transalkylation catalyst. The catalyst in the reactive or unreactive guard bed is therefore subject to more frequent regeneration and/or replacement than the remainder of the alkylation or transalkylation catalyst, and hence the guard bed is typically provided with a by-pass circuit so that the alkylation feed(s) may be fed directly to the series connected reaction zones in the reactor while the guard bed is out of service. The reactive or unreactive guard bed may be operated in co-current upflow or downflow operation.

The reaction zone(s) used in the process of the present invention is typically operated so as to achieve essentially complete conversion of the alkene. However, for some applications, it may be desirable to operate at below 100% alkene conversion. The employment of a separate finishing reactor downstream of the reaction zone(s) may be desirable under certain conditions. The finishing reactor would also contain alkylation or transalkylation catalyst, which could be the same or different from the catalyst used in other reaction zones in the alkylation or transalkylation reactor(s) and may be maintained under at least partially liquid phase or alternately vapor phase alkylation or transalkylation conditions. The polyalkylated aromatic compounds in the effluents may be separated for transalkylation with alkylatable aromatic compound(s). The alkylated aromatic compound is made by transalkylation between polyalkylated aromatic compounds and the alkylatable aromatic compound.

The alkylation or transalkylation reactor(s) used in the process of the present invention may be highly selective to the desired monoalkylated product, such as ethylbenzene, but typically produces at least some polyalkylated species. In one embodiment, the effluent from the final alkylation reaction zone is subjected to a separation step to recover polyalkylated aromatic compound(s). In another embodiment, at least a portion of the polyalkylated aromatic compound is supplied to a transalkylation reactor which may be separate from the alkylation reactor. The transalkylation reactor produces an effluent which contains additional monoalkylated product by reacting the polyalkylated species with an alkylatable aromatic compound. At least a portion of these effluents may be separated to recover the alkylated aromatic compound (monoalkylated aromatic compound and/or polyalkylated aromatic compound).

Particular conditions for carrying out the alkylation of benzene with ethylene at least partially in liquid phase may have a temperature of from about 120° C. to 285° C., preferably, a temperature of from about 150° C. to 260° C., a pressure of 689 to 4601 kPa-a, preferably, a pressure of 1500 to 4137 kPa-a, a WHSV based on total ethylene and total catalyst for overall reactor of 0.1 to 10 hr$^{-1}$, preferably, 0.2 to 2 hr$^{-1}$, more preferably, 0.5 to 1 hr$^{-1}$, or a WHSV based on both total ethylene and benzene, and total catalyst for overall reactor of 10 to 100 hr$^{-1}$, preferably, 20 to 50 hr$^{-1}$, and a molar ratio of benzene to ethylene from about 1 to about 10.

Particular conditions for carrying out the at least partially in liquid phase alkylation of benzene with propylene may include a temperature of from about 80° C. to 160° C., a pressure of about 680 to about 4800 kPa-a; preferably from about 100° C. to 140° C. and pressure of about 2000 to 3000 kPa-a, a WHSV based on propylene of from about 0.1 about 10 hr$^{-1}$, and a molar ratio of benzene to ethylene from about 1 to about 10.

Where the alkylation system includes a reactive guard bed, it is maintained under at least partial in liquid phase conditions. The guard bed will preferably operate at a temperature of from about 120° C. to 285° C., preferably, a temperature of from about 150° C. to 260° C., a pressure of 689 to 4601 kPa-a, preferably, a pressure of 1500 to 4137 kPa-a, a WHSV based on total ethylene and the total amount of catalyst for the overall reactor of 0.1 to 10 hr$^{-1}$, preferably, 0.2 to 2 hr$^{-1}$, more preferably, 0.5 to 1 hr$^{-1}$, or a WHSV based on both total ethylene and total benzene, and the total amount of catalyst for the overall reactor of 10 to 100 hr$^{-1}$, preferably, 20 to 50 hr$^{-1}$, and a molar ratio of benzene to ethylene from about 1 to about 10.

The transalkylation reaction may take place under at least partially in liquid phase conditions. Particular conditions for carrying out the at least partially in liquid phase transalkylation of polyalkylated aromatic compound(s), e.g., polyethylbenzene(s) or polyisopropylbenzene(s), with benzene may include a temperature of from about 100° C. to about 300° C., a pressure of 696 to 4137 kPa-a, a WHSV based on the weight of the polyalkylated aromatic compound(s) feed to the alkylation reaction zone of from about 0.5 to about 100 hr$^{-1}$ and a molar ratio of benzene to polyalkylated aromatic compound(s) of from 1:1 to 30:1, preferably, 1:1 to 10:1, more preferably, 1:1 to 5:1.

In another embodiment, the transalkylation reaction may take place under vapor phase conditions. Particular conditions for carrying out the vapor phase transalkylation of polyalkylated aromatic compound(s), e.g., polyethylbenzene(s) or polyisopropylbenzene(s), with benzene may include a temperature of from about 350° C. to about 450° C., a pressure of 696 to 1601 kPa-a, a WHSV based on the weight of the polyalkylated aromatic compound(s) feed to the reaction zone of from about 0.5 to about 20 hr$^{-1}$, preferably, from about 1 to about 10 hr$^{-1}$, and a molar ratio of benzene to polyalkylated aromatic compound(s) of from 1:1 to 5:1, preferably, 2:1 to 3:1.

Industrial Applications

The catalyst composition of this disclosure is useful for hydrocarbon conversion processes, for example, benzene alkylation with ethylene or propylene. In some embodiments, the catalyst composition of this disclosure (MCM-49 molecular sieve and titania) has a catalytic activity at least 1%, preferably at least 5%, even more preferably at least 10%, and most preferably at least 20% higher than a catalytic activity of a catalyst composition for the same amount of the MCM-49 molecular sieve without the titania under equivalent conditions.

In some embodiments, this disclosure relates to:

Paragraph 1: A catalyst composition comprising:
(a) a MCM-22 family material; and
(b) a binder comprising a titanium compound in the range from about 1 wt. % to about 35 wt. % based on the weight of said catalyst composition.

Paragraph 2: The catalyst composition of Paragraph 1, wherein said titanium compound comprises at least one of titanium oxide, titanium hydroxide, titanium sulfate, titanium phosphate, or any combination thereof.

Paragraph 3: The catalyst composition of any preceding Paragraph further comprising additional crystalline MCM-22 family molecular sieve, wherein said crystalline MCM-22 family molecular sieve comprises at least one of MCM-22, MCM-36, MCM-49, MCM-56, ITQ-1, ITQ-2, ITQ-30, or any combination thereof.

Paragraph 4: The catalyst composition of any preceding Paragraph further comprising a molecular sieve having a framework type of at least one of FAU, *BEA, MFI, MTW, or any combination thereof.

Paragraph 5: The catalyst composition of any preceding Paragraph wherein said MCM-22 family material comprises at least one of MCM-22, MCM-36, MCM-49, MCM-56, EMM-10 family molecular sieve, ITQ-1, ITQ-2, and ITQ-30.

Paragraph 6: The catalyst composition of any preceding Paragraph having at least 65 wt. % of said MCM-22 family material based on the weight of said catalyst composition.

Paragraph 7: The catalyst composition of any preceding Paragraph having at least 60 wt. % of said crystalline MCM-49 molecular sieve based on the eight of said catalyst composition.

Paragraph 8: The catalyst composition of any preceding Paragraph, wherein said binder has less than or equal to 30 wt. % of said titanium compound based on the weight of said catalyst composition.

Paragraph 9: The catalyst composition of any preceding Paragraph, wherein said binder has less than or equal to 20 wt. % of said titanium compound based on the weight of said catalyst composition.

Paragraph 10: The catalyst composition of any preceding Paragraph further comprising at least 1 wt. % aluminum compound based on the weight of said catalyst composition.

Paragraph 11: The catalyst composition of Paragraph 10 wherein said aluminum compound comprises at least one of aluminum oxide, aluminum hydroxide, aluminum sulfate, aluminum phosphate, or any combination thereof.

Paragraph 12: The catalyst composition of any preceding Paragraph further comprising at least 5 wt. % of a molecular sieve having a *BEA framework type based on the weight of said catalyst composition weight.

Paragraph 13: A process for alkylating an aromatic hydrocarbon with an alkylating agent to produce an alkylated aromatic product, said process comprising contacting said aromatic hydrocarbon and said alkylating agent with the catalyst composition of any preceding Paragraph under alkylation conditions effective to alkylate said aromatic hydrocarbon with said alkylating agent to form an effluent comprising said alkylated aromatic product.

Paragraph 14: The process of Paragraph 13, wherein said aromatic hydrocarbon comprises benzene, said alkylating agent comprises ethylene, and said alkylated aromatic product comprise ethylbenzene.

Paragraph 15: The process of Paragraph 13, wherein said aromatic hydrocarbon comprises benzene, said alkylating agent comprises propylene, and said alkylated aromatic product comprise cumene.

Paragraph 16: The process of any one of Paragraphs 13-15, wherein the amount of said alkylated aromatic product produced is at least 1 wt. % greater than the alkylated aromatic product in the effluent produced by contacting an alumina-bound-catalyst composition having a binder consisting of alumina and having same weight ratio of the molecular sieve over the alumina-bound-catalyst composition when compared under equivalent alkylation conditions.

Paragraph 17: A process for preparing the catalyst composition of any one of Paragraphs 1-12 comprising:
(a) providing said MCM-22 family material and said binder comprising at least 1 wt. % of a titanium compound to form a mixture; and
(b) forming said mixture into said catalyst composition.

Paragraph 18: The process of Paragraph 16, wherein said forming step comprises extruding.

Paragraph 19: The process of any one Paragraphs 16-17, wherein said catalyst composition has a shape of quadrulobe.

Paragraph 20: The process of any one Paragraphs 16-19, wherein said catalyst composition further at least 5 wt. % of a molecular sieve having a *BEA framework type based on the weight of said catalyst composition.

These and other facets of the present invention are exemplified by the following Examples.

Testing Procedures
Feed Pretreatment

Benzene (99.96 wt. %) was obtained from the ExxonMobil Baytown Chemical plant. The benzene was passed through a pretreatment vessel (2 L Hoke vessel) containing absorbent materials from inlet to outlet. All absorbent feed pretreatment materials were dried in a 260° C. oven for 12 hours before using.

Polymer grade propylene was obtained from Scott Specialty Gases (Pasadena, Tex., USA). Propylene was passed through a 300 ml vessel containing absorbents which were dried in a 260° C. oven for 12 hours before using.

Ultra high purity grade Nitrogen was obtained from Scott Specialty Gases.

Nitrogen was passed through a 300 ml vessel containing absorbents which were dried at 260° C. for 12 hours before using. Catalyst Preparation and Loading MCM-22 catalyst was prepared according to U.S. Pat. No. 4,954,325, the whole content of which is incorporated herein as reference. MCM-49 catalyst was prepared according to U.S. Pat. No. 5,236,575, the whole content of which is incorporated herein as reference.

Titania was obtained from Degussa Corporation (Degussa AG, PO Box 30 20 43, 40402 Dusseldorf, Germany) as AEROXIDE® $TiO_2$ P25 (hereinafter "P25 titania"). Alumina was obtained from UOP LLC (UOP LLC, 25 East Algonquin Road, Des Plaines, Ill. 60017-5017, U.S.A.) as Versal-300 or Versal-200 alumina Extrusion was performed on Bonnot single screw extruder (The Bonnot Company, 1520 Corporate Woods Parkway, Uniontown, Ohio 44685, U.S.A.). Organic extrusion aid, poly vinyl alcohol (hereinafter "PVA") was obtained from Celanese as Celvol 603. Scanning Electron Microscope (SEM) images were obtained on a HITACHI 54800 Field Emission Scanning Electron Microscope (SEM).

One gram of catalyst was dried in air at 260° C. for 2 hours. The catalyst was removed immediately after drying. The bottom of a catalyst basket was packed with quartz chips followed by loading of 0.5 grams of catalyst into basket on top of the quartz chips. The catalyst was then covered by additional quartz chips. The catalyst basket containing the catalyst and quartz chips was dried at 260° C. in air for about 16 hours.

Before each experiment the reactor and all lines were cleaned with a suitable solvent (such as toluene) followed by flowing of air after cleaning to remove all cleaning solvent. The catalyst basket containing the catalyst and quartz chips was placed in reactor immediately after drying.

A 300 ml Parr® batch reaction vessel (Series 4563 mini Bench top reactor with a static catalyst basket, Parr Instrument Company, Moline, Ill. USA) equipped with a stir rod and static catalyst basket was used for the activity and selectivity measurements. The reaction vessel was fitted with two removable vessels for the introduction of benzene and propylene respectively.

Catalytic Activity and Selectivity

The activity and selectivity of a catalyst were measured based on benzene alkylation with propylene. Catalytic activity was calculated using the second order rate constant for the formation of cumene under the reaction conditions (temperature 130° C. and pressure 2170 kPa-a). Reaction rate-constants were calculated using methods known to those skilled in the art. See "Principles and Practice of Heterogeneous Catalyst", J. M. Thomas, W. J. Thomas, VCH, 1st Edition, 1997, the disclosure of which is incorporated herein by reference. Catalyst selectivity was calculated using the weight ratio of cumene produced over di-isopropyl benzenes produced under the reaction conditions (temperature 130° C. and pressure 2170 kPa-a).

The reactor was purged with 100 ml/min of the treated ultra high purity nitrogen, $N_2$, for 2 hours at 170° C. Then, the reactor temperature was reduced to 130° C. under nitrogen flow. All inlets and outlets of the reactor were closed off afterward. Pretreated benzene (156.1 gram) was transferred into the reactor under 791 kPa-a ultra high purity nitrogen blanket. The reactor was stirred at 500 rpm for 1 hour. Pretreated liquid propylene (28.1 gram) under 2170 kPa-a ultra high purity nitrogen is then transferred to the reactor. The reactor was maintained at 2170 kPa-a by the 2170 kPa-a ultra high purity nitrogen. Liquid samples were taken at 15, 30, 60, 120, 180, and 240 min after addition of the propylene.

EXAMPLE 1

MCM-49 was extruded in a 5.08 cm (2") extruder according to the following formulation: mixture of MCM-49 crystal and P25 titania (weight ratio 80:20) extruded with 1 wt. % PVA (based on the combined weight of MCM-49 crystal, P25 titania, and PVA) to 0.127 cm (1/20") extrudate. This extrudate was then pre-calcined in nitrogen at 510° C., ammonium exchanged with ammonium nitrate, and calcined in an air/$N_2$ mixture at 538° C. The catalyst of Example 1 was tested in the batch autoclave liquid phase benzene alkylation test and results are listed in Table 1.

EXAMPLE 2

MCM-49 was extruded in a 5.08 cm (2") extruder according to the following formulation: mixture of MCM-49 crystal, P25 titania, and Versal-300 alumina (weight ratio 80:10:10) extruded with 1 wt. % PVA (based on the combined weight of MCM-49 crystal, P25 titania, Versal-300 alumina, and PVA) to 0.127 cm (1/20") extrudate. This extrudate was then pre-calcined in nitrogen at 510° C., ammonium exchanged with ammonium nitrate, and calcined in an air/$N_2$ mixture at 538° C. The catalyst of Example 2 was tested in the batch autoclave liquid phase benzene alkylation test and results are listed in Table 1.

EXAMPLE 3 (COMPARATIVE EXAMPLE)

MCM-49 was extruded in a 12.7 cm (5") extruder according to the following formulation: mixture of MCM-49 crystal and Versal-300 alumina (weight ratio 80:20) extruded with 2 wt. % PVA and 2 wt. % nitric acid (based on the combined weight of MCM-49 crystal, Versal-300 alumina, nitric acid and PVA) to 0.127 cm (1/20") extrudate. This extrudate was then pre-calcined in nitrogen at 510° C., ammonium exchanged with ammonium nitrate, and calcined in an air/$N_2$ mixture at 538° C. The catalyst of Example 3 was tested in the batch autoclave liquid phase benzene alkylation test and results are listed in Table 1.

EXAMPLE 4

MCM-49 was extruded in a 5.08 cm (2") extruder according to the following formulation: mixture of MCM-49 crystal, P25 titania, and Versal-200 alumina (weight ratio 60:20:20) extruded with 1 wt. % PVA (based on the combined weight of MCM-49 crystal, P25 titania, Versal-200 alumina, and PVA) to 0.127 cm (1/20") extrudate. This extrudate was then pre-calcined in nitrogen at 510° C., ammonium exchanged with ammonium nitrate, and calcined in an air/$N_2$ mixture at 538° C. The catalyst of Example 4 was tested in the batch autoclave liquid phase benzene alkylation test and results are listed in Table 1.

EXAMPLE 5 (COMPARATIVE EXAMPLE)

MCM-49 was extruded in a 5.08 cm (2") extruder according to the following formulation: mixture of MCM-49 crystal and Versal-200 alumina (weight ratio 60:40) extruded into 0.127 cm (1/20") extrudate. This extrudate was then pre-calcined in nitrogen at 510° C., ammonium exchanged with ammonium nitrate, and calcined in an air/$N_2$ mixture at 538° C. The catalyst of Example 5 was tested in the batch autoclave liquid phase benzene alkylation test and results are listed in Table 1.

The catalytic activity of examples 1 and 2 were normalized to example 3 (as 100). The catalytic activity of example 4 was normalized to example 5 (as 100). The results show examples having titania have higher activities than examples without titania.

TABLE 1

Benzene Alkylation Testing results for Examples 1-5

| Example | 1 | 2 | 3 | 4 | 5 |
|---|---|---|---|---|---|
| MCM-49:$TiO_2$:$Al_2O_3$ (weight ratios) | 80:20:0 | 80:10:10 | 80:0:20 | 60:20:20 | 60:0:40 |
| Normalized Activity | 140 | 166 | 100 | 120 | 100 |

EXAMPLE 6

MCM-22 was extruded in a 12.7 cm (2") extruder according to the following formulation: mixture of MCM-22 crystal and P25 titania (weight ratio 60:40) extruded to 0.159 cm (1/16") extrudate. This extrudate was then pre-calcined in nitrogen at 510° C., ammonium exchanged with ammonium nitrate, and calcined in an air/N$_2$ mixture at 538° C. The catalyst of Example 6 was tested in the batch autoclave liquid phase benzene alkylation test and results are listed in Table 2.

EXAMPLE 7 (COMPARATIVE EXAMPLE)

MCM-22 was extruded in a 5.08 cm (5") extruder according to the following formulation: mixture of MCM-22 crystal and Versal-200 alumina (weight ratio 65/35) extruded into 0.159 cm (1/16") extrudate. This extrudate was then pre-calcined in nitrogen at 510° C., ammonium exchanged with ammonium nitrate, and calcined in an air/N$_2$ mixture at 538° C. The catalyst of Example 7 was tested in the batch autoclave liquid phase benzene alkylation test and results are listed in Table 2.

The catalytic activity of example 6 was normalized to example 7 (as 100). The results show the example having titania has about 92% of the activity of the example 7. However, after the catalytic activities were normalized to the same MCM-22 molecular sieve content, the example having titania has similar activity to an example without titania.

TABLE 2

Benzene Alkylation Testing results for Examples 6-7

|  | Example 7 | Example 8 |
|---|---|---|
| MCM-22:TiO$_2$:Al$_2$O$_3$ (weight ratios) | 60:40:0 | 65:0:35 |
| Normalized Activity | 92 | 100 |
| Normalized Activity (to same molecular sieve content) | 99.7 | 100 |

EXAMPLE 8

Zeolite Beta was extruded in a 12.7 cm (2") extruder according to the following formulation: mixture of Beta crystal and P25 titania (weight ratio 80:20) was extruded to form a 0.127 cm (1/20") extrudate. This extrudate was then pre-calcined in nitrogen at 510° C., ammonium exchanged with ammonium nitrate, and calcined in an air/N$_2$ mixture at 538° C. The catalyst of Example 8 was tested in the batch autoclave liquid phase benzene alkylation test and results are listed in Table 3 normalized to the catalyst from comparative example 10.

EXAMPLE 9 (Comparative Example)

Zeolite Beta was extruded in a 12.7 cm (2") extruder according to the following formulation: mixture of Beta crystal and Versal-300 alumina (weight ratio 80:20) was extruded to form a 0.127 cm (1/20") extrudate. This extrudate was then pre-calcined in nitrogen at 510° C., ammonium exchanged with ammonium nitrate, and calcined in an air/N$_2$ mixture at 538° C. The catalyst of Example 9 was tested in the batch autoclave liquid phase benzene alkylation test and results are listed in Table 3.

TABLE 3

Benzene Alkylation Testing results for Example 9

|  | Example 8 | Example 9 |
|---|---|---|
| Beta:TiO$_2$:Al$_2$O$_3$ (weight ratios) | 80:20:0 | 80:0:20 |
| Normalized Activity | 76 | 100 |

The results show that there is no activity enhancement for zeolite beta with a binder having titanium compound.

EXAMPLE 10 (COMPARATIVE EXAMPLE)

MCM-22 was extruded according to the following formulation: mixture of MCM-22 crystal and Versal-300 Alumina (weight ratio 80:20) extruded with 1 wt. % PVA (based on the combined weight of MCM-22 crystal, Alumina, and PVA) to 0.127 cm (1/20") extrudate. This extrudate was then pre-calcined in nitrogen at 510° C., ammonium exchanged with ammonium nitrate, and calcined in an air/N$_2$ mixture at 538° C. The catalyst of Example 10 was tested in the batch autoclave liquid phase benzene alkylation test and results are listed in Table 4.

EXAMPLE 11

MCM-22 was extruded according to the following formulation: mixture of MCM-22 crystal and P25 Titania (weight ratio 80:20) extruded with 1 wt. % PVA (based on the combined weight of MCM-22 crystal, Titania, and PVA) to 0.127 cm (1/20") extrudate. This extrudate was then pre-calcined in nitrogen at 510° C., ammonium exchanged with ammonium nitrate, and calcined in an air/N$_2$ mixture at 538° C. The catalyst of Example 11 was tested in the batch autoclave liquid phase benzene alkylation test and results are listed in Table 4.

TABLE 4

Benzene Alkylation Testing results for Examples 10-12

| Example | 10 | 11 |
|---|---|---|
| MCM-22:TiO$_2$:Al$_2$O$_3$ (weight ratios) | 80:0:20 | 80:20:0 |
| Normalized Activity | 100 | 135 |

The data indicates activity improvement for the addition of titanium to both MCM-22 and MCM-49 catalyst. The activity improvement is more profound when the amount of titanium or the combined about of titanium and alumina is less than or equal to 35 wt. % or when the amount of MCM-49 or MCM-22 is more than 65 wt. %. Not intended to be bound by any theory, we believe that the surprisingly result of activity improvement at low level of titanium compound or high level of MCM-22 family material, such as MCM-22 or MCM-49 is related to the mass transfer limited liquid phase nature for benzene alkylation with propylene and/or ethylene.

We claim:
1. A catalyst composition comprising:
   (a) a MCM-22 family material; and
   (b) a binder comprising a titanium compound in the range from about 1 wt. % to about 35 wt. % based on the weight of said catalyst composition, wherein said titanium compound has anatase and rutile phases.

2. The catalyst composition of claim 1, wherein said titanium compound comprises at least one of titanium oxide, titanium hydroxide, titanium sulfate, titanium phosphate, or any combination thereof.

3. The catalyst composition of claim 1, further comprising a different, second crystalline MCM-22 family molecular sieve, wherein said second crystalline MCM-22 family molecular sieve comprises at least one of MCM-36, MCM-49, MCM-56, EMM-10 family molecular sieve, ITQ-1, ITQ-2, ITQ-30, or any combination thereof.

4. The catalyst composition of claim 1, further comprising a molecular sieve having a framework type of at least one of FAU, *BEA, MFI, MTW, or any combination thereof.

5. The catalyst composition of claim 1, wherein said MCM-22 family material comprises at least one of MCM-22, MCM-36, MCM-49, MCM-56, EMM-10 family molecular sieve, ITQ-1, ITQ-2, and ITQ-30.

6. The catalyst composition of claim 1, having at least 65 wt. % of said MCM-22 family material based on the weight of said catalyst composition.

7. The catalyst composition of claim 1, having at least 80 wt. % of said crystalline MCM-49 molecular sieve based on the eight of said catalyst composition.

8. The catalyst composition of claim 1, wherein said binder has less than or equal to 30 wt. % of said titanium compound based on the weight of said catalyst composition.

9. The catalyst composition of claim 1, wherein said binder has less than or equal to 20 wt. % of said titanium compound based on the weight of said catalyst composition.

10. The catalyst composition of claim 1, further comprising at least 1 wt. % aluminum compound based on the weight of said catalyst composition.

11. The catalyst composition of claim 10, wherein said aluminum compound comprises at least one of aluminum oxide, aluminum hydroxide, aluminum sulfate, aluminum phosphate, or any combination thereof.

12. The catalyst composition of claim 1, further comprising at least 5 wt. % of a molecular sieve having a *BEA framework type based on the weight of said catalyst composition weight.

* * * * *